April 20, 1937. F. C. RAFFEL Plant Pat. 246
ROSE
Filed Oct. 24, 1936
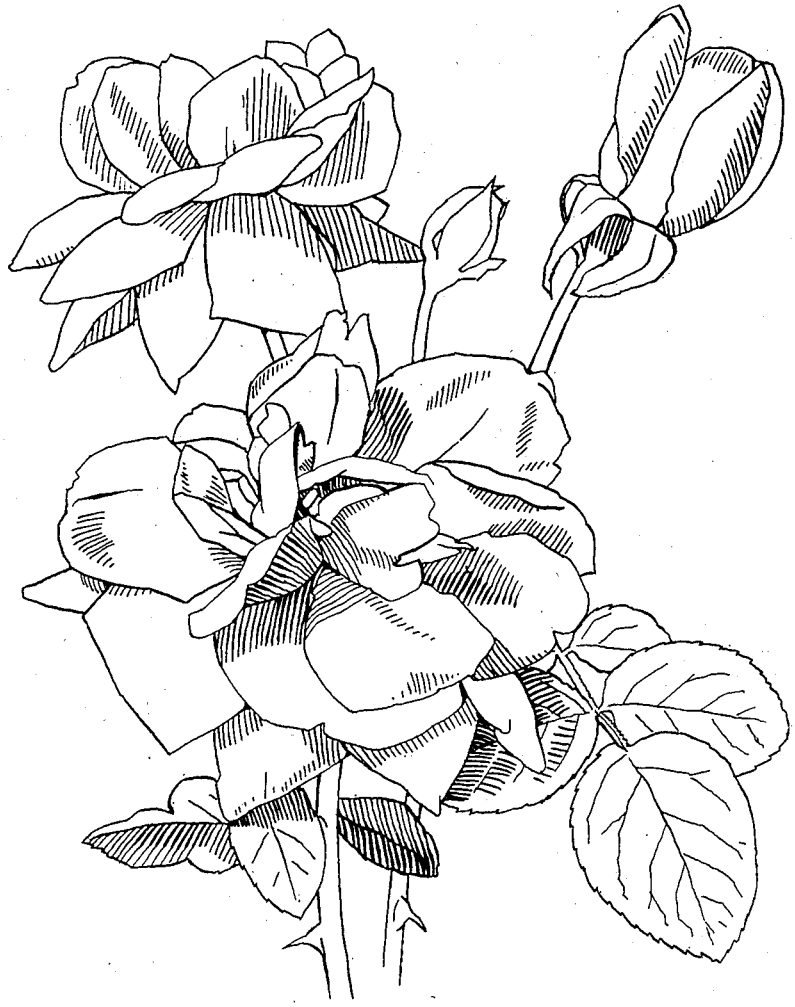
INVENTOR
F. C. Raffel
BY
ATTORNEY Patented Apr. 20, 1937

Plant Pat. 246

UNITED STATES PATENT OFFICE

246

ROSE

Frank C. Raffel, Stockton, Calif.

Application October 24, 1936, Serial No. 107,327

1 Claim. (Cl. 47—61)

This discovery relates generally to roses, and particularly and specifically relates to a climbing hybrid tea rose having the same general characteristics as that variety of rose known as the "Climbing Golden Emblem" but which is distinguished therefrom mainly by the fullness of its flowers, and persistence of the color of the flowers.

On or about October 1, 1933 I gathered seeds from a Climbing Golden Emblem rose which grows in my nursery at Stockton, California. The seeds thus gathered were then planted, precaution being taken to prevent other seeds from being mixed therewith, and on or about April 1st, 1935, the resultant seedling plants began to bloom. At that time I recognized and discovered the new variety of rose herein described and since its discovery I have successfully asexually reproduced the new variety and have determined that the reproduced plants bear flowers having the same fullness of bloom and persistence of color as the original plant of the new variety. As the flowers of the parent rose from which the seeds were obtained were not artificially polinated, the true parentage of the new variety is unknown.

I refer now in more detail to the plant and its flowers:

*Habit of growth.*—The plant is upright and climbing as well as being quite vigorous. The growth is more branchy and graceful and the branches are solid as compared to the parent variety. The bark of new growth of the stems is green. There are a normal amount of thorns; the thorns being slightly smaller than those found on the parent variety of rose.

*Character of foliage.*—The foliage of the plant is normal, of normal green color, and is very glossy. The leaves are of medium size and are resistant to mildew under ordinary weather conditions. The leaves are slightly smaller than those of the parent variety.

*Flower.*—The flower buds are slightly shorter than those of the parent plant; the buds being a golden yellow color splashed with red on the outside of the outer petals. The flowers are a golden yellow in color and after blooming do not fade perceptibly as do the flowers of the parent "Climbing Golden Emblem" variety. The flowers are four to four and one-half inches in diameter when open and bloom freely at intervals from April through November having from seventy to eighty petals in the spring months and slightly less in the summer and fall months. The flowers are thus characterized by more fullness of bloom and a longer free blooming period than the parent variety.

The plant is also a prolific bloomer; the flowers have a moderate fragrance; they are usually borne singly although occasionally two or three flowers will be found on a single stem; the flowers last two or three days longer than those of the parent variety, and they fall clean. Three year old plants have not as yet developed any seed pods.

In summary, my newly discovered rose is distinguished from the parent variety, "Climbing Golden Emblem", by reason of its fullness of bloom; the lasting quality of the flowers, the continued free blooming at intervals into the fall months and the persistence of the golden yellow color even when exposed directly to the sun. The flowers of the parent variety fade from yellow to white soon after blooming.

Of course, the rose plant and its flower, above described, may vary in slight details depending on soil and climatic conditions.

Having thus described my discovery, I claim:

The climbing hybrid tea rose herein described characterized by its fullness of bloom and persistence of color as compared with the "Climbing Golden Emblem" variety.

FRANK C. RAFFEL.